United States Patent [19]

Smith

[11] Patent Number: 4,504,282

[45] Date of Patent: Mar. 12, 1985

[54] PRODUCTION OF HYDROCARBONS

[75] Inventor: John W. Smith, Germantown, Tenn.

[73] Assignee: Memphis State University, Memphis, Tenn.

[21] Appl. No.: 266,388

[22] Filed: May 20, 1981

[51] Int. Cl.$^3$ ............................................. C10J 3/00
[52] U.S. Cl. ..................................... 48/197 R; 48/210
[58] Field of Search ..................... 423/439; 585/733; 48/197 R, 210

[56] References Cited

U.S. PATENT DOCUMENTS 4,184,852  1/1980  Russ ................................. 48/197 R
4,310,334  1/1982  Waldron ........................... 48/197 R

OTHER PUBLICATIONS

Singleton et al., "Reactions Between Manganous Oxide, Graphite, and Manganese Carbide", Bureau of Mines Report 6567, 1964, pp. 2, 5.

Kosolapova, *Carbides*, Plenum Press, 1971, pp. 55–57, 167–175, 188, 189, 245, 246, 250–252.

*Primary Examiner*—Peter F. Kratz
*Attorney, Agent, or Firm*—Polster, Polster and Lucchesi

[57] ABSTRACT

A method of producing a source of rich (in the general range of 900 BTU per cubic foot) gaseous fuel, and a method of producing a rich gaseous fuel, both include reducing metallic manganese or a mixture of metals in which manganese predominates and carbonaceous material to a powder finer than 200 mesh, mixing the powders in a proportion by weight between 1 to 1 and 4 to 1 manganese to carbonaceous material (available carbon), and heating the mixture, in a reducing atmosphere, to a temperature of between 600° and 950° C. to substantial equilibrium by completion of reaction, generally for a period of about forty minutes. The production of gaseous fuel includes the step of treating the source material with a reactant taken from the group consisting of steam and a mildly acidic solution. The source material residue is then recycled.

8 Claims, No Drawings

PRODUCTION OF HYDROCARBONS

BACKGROUND OF THE INVENTION

The production of metal carbides and the generation of hydrogen and gaseous hydrocarbons by reacting the carbides with water or an acid solution is an old art. Acetylene produced from calcium carbide was used as an illuminating gas in automobiles before electric lights were employed, and the patent literature relating to the production of various carbides goes back nearly a hundred years (see Whitehead U.S. Pat. No. 555,796). A Johnson U.S. Pat. No. 2,686,819, discloses the production of methane by forming ferrous carbide by reacting ferrosic oxide with carbon monoxide, and then reacting the carbide with hydrogen. Johnson suggests that any metal capable of forming a carbide may be utilized in this synthesis. Russ, U.S. Pat. No. 4,184,852, discloses forming a mixture of metastable carbides and stable carbides by heating metals forming these carbides in the presence of carbon, and then hydrolizing the carbides to produce natural gas-type carbons. In accordance with the Russ disclosure, "The carbides of this invention must contain at least one metastable, and at least one stable carbide-forming metal element each."

It has been found that, as distinguished from the Russ method, a fuel source can be produced that generates less than 10% hydrogen, less than 50% methane, and the balance substantially all saturated aliphatic hydrocarbons (e.g., ethane, propane, and butane), when treated with steam or a mildly acidic solution, by using manganese as the sole or as the preponderant metallic constituent of the source under the conditions described.

One of the objects of this invention is to provide a fuel source by which a rich (in the general range of 900 BTU per cubic foot) gaseous fuel can be generated.

Other objects will become apparent to those skilled in the art in the light of the following description.

SUMMARY OF THE INVENTION

In accordance with this invention, generally stated, a source of gaseous fuel is produced by reducing metallic manganese or a mixture of aluminum, iron and manganese in which the manganese predominates, to a powder finer than 200 mesh, reducing carbonaceous material to a similar fineness, mixing the powders in a proportion by weight of between 1 to 1 and 4 to 1 manganese to carbonaceous material, and heating the mixture, in a reducing atmosphere, to a temperature between 600° and 950° C. for a length of time to accomplish substantial completion of reaction at that temperature, generally, at atmospheric pressure, for a period of about forty minutes. A rich (in the general range of 900 BTU per cubic foot) gaseous fuel is produced from the source material by treating the source material with steam or a mildly acidic solution or a mixture of the two. The resultant gas contains less than 10% hydrogen, less than 50% methane, and the remainder substantially all ethane, propane and butane. The source material residue is then recycled. In recycling, make-up metal is used as required, but the conditions under which the original metal was reacted with the carbon produce suitable source material from the residue (sometimes referred to as spent material) or the mixture of spent material and make-up metal.

DESCRIPTION OF THE PREFERRED EMBODIMENT

In the preferred embodiment of process of producing a fuel source of this invention, metallic manganese is reduced to a fineness to pass 300 mesh. A carbonaceous material, in this embodiment bituminous coal with an available carbon content of 60%, is reduced to a similar fineness. The powdered metal and the powdered coal are mixed in the proportion by weight of 2 to 1 manganese to coal and placed in a heated atmosphere under reducing conditions. In this embodiment, the mixture is placed in a closed container, externally heated. In the absence of oxygen, the heating of the coal will produce a reducing atmosphere, but carbon monoxide or other reducing gas or an inert gas blanket may be introduced to the compartment in which the mixture is being heated. The mixture is heated to a minimum of 600° C. and no more than 950° C., the optimum temperature being approximately 740° C., for forty minutes. At the end of the forty minutes, the source material is removed from the heated area and placed in a reactor where, in this illustrative embodiment, it is treated with a mild (5% by weight) aqueous hydrochloric acid solution, by injecting the 5% acid solution from below the bed of material in an amount at least 10% by weight of the source material. The yield of gas increases with the injection of more acid, up to a 1 to 1 weight ratio of acid solution to source material, but at a reduced rate above 10%. The resultant gas is typically 5% hydrogen, 35% methane, 10% ethane, 20% propane and 30% butane.

The residue from the reactor consists largely of fixed carbon, manganese oxides and unreacted materials from the coal. This residue is dried to remove any water from the mixture, recombined with fresh carbon and makeup metal as required, and recycled. The metal oxides will be reduced by the carbon, and the resulting carbon monoxide will provide the reducing atmosphere in the closed compartment.

In another embodiment of this invention, aluminum, iron and manganese, all reduced to a powder of a fineness between 200 and 325 mesh, in the approximate ratio of 1 to 1 to 2 aluminum to iron to manganese, by weight, are mixed with carbon, in this illustrative embodiment coal with an effective carbon content of 60%, reduced to the same fineness, in the ratio of 1.4 to 1 by weight of manganese to coal. The mixture is placed in a muffle furnace and heated to 740° C. for forty minutes. The source mixture is then removed from the furnace and reacted with a 5% aqueous hydrochloric acid solution. The resulting gas has the following composition: Hydrogen 5%, methane 20%, ethane 15%, propane 30%, and butane 30%, as determined by infrared and gas chromatographic analyses.

As in the first embodiment, the residue from the reactor can be dried, recombined with fresh carbon and makeup metals as required, and recycled.

Instead of the mild acid solution, saturated steam or a mixture of saturated steam and mild acid solution may be used to react with the source mixture to form gas of substantially the same composition. Other acids, such as sulphuric, can be employed in substantially the same hydrogen ion concentration, instead of hydrochloric acid, but hydrochloric acid has been found to produce the best results and is the preferred acid. Other carbonaceous materials, including carbonized wastes, as well as coke, charcoal and the like, can be employed, although coal is the preferred source of carbon. The reducing atmosphere can be provided by using a tightly closed compartment or a covering layer of inert material. In producing the source material, the heating can be extended beyond forty minutes, although a period of forty minutes after the material has reached the desired temperature has been found to be sufficient, the only criterion being that the reaction produced under the conditions described be taken to substantial completion. The temperature at which the source material is produced can vary from 600° to about 950° C., but the optimum temperature has been found to be 740° C., and heating substantially above that temperature is unnecessary and undesirable. The use of more than a 1 to 1 ratio of carbon to powdered metal does not appear to affect the production of the fuel source one way or the other, so that the use of more than a 1 to 1 ratio is simply wasteful. The fineness of the powders from which the source material is made is important. Preferably the powders will pass through a 300 mesh screen, and they must pass through a 200 mesh screen.

Numerous other variations in the process of this invention, within the scope of the appended claims, will occur to those skilled in the art in the light of the foregoing disclosure.

I claim:

1. The method of producing a source of gaseous fuel comprising reducing metallic manganese and carbonaceous material to powder finer than 200 mesh, mixing said manganese powder and carbonaceous material, and heating said mixture, in a reducing atmosphere, to a temperature not less than 600° nor more than 950° C. to substantial equilibrium by completion of reaction.

2. The method of claim 1 wherein the carbonaceous material is coal.

3. The method of claim 1 wherein the mixture is maintained at a temperature of about 740° C. for about forty minutes.

4. The method of producing a gas containing less than 10% hydrogen, less than 50% methane, and the balance substantially all saturated aliphatic hydrocarbons comprising producing a source of gaseous fuel by reducing metallic manganese and carbonaceous material to powder finer than 200 mesh, mixing said manganese powder and carbonaceous material, and heating said mixture, in a reducing atmosphere, to a temperature not less than 600° nor more than 950° C. to substantial equilibrium by completion of reaction, and treating said source material with a reactant taken from the group consisting of saturated steam, a mildly acidic aqueous solution and a mixture of saturated steam and mildly acidic aqueous solution.

5. The method of producing a source of gaseous fuel comprising reducing to a powder finer than 200 mesh a carbonaceous material and a major proportion of metallic manganese and a minor proportion of iron and aluminum, mixing said metallic powders with said carbonaceous material, and heating said mixture, in a reducing atmosphere, to a temperature not less than 600° C. nor more than 950° C. to substantial equilbrium by completion of reaction.

6. The method of claim 5 wherein the carbonaceous material is coal.

7. The method of claim 5 wherein the mixture is maintained at a temperature of about 740° C. for about forty minutes.

8. The method of producing a gas containing less than 10% hydrogen, less than 50% methane, and the balance substantially all saturated aliphatic hydrocarbons comprising producing a source of gaseous fuel by reducing to a powder finer than 200 mesh a carbonaceous material and a major proportion of metallic manganese and a minor proportion of iron and aluminum, mixing said metallic powders with said carbonaceous material, and heating said mixture, in a reducing atmosphere, to a temperature not less than 600° C. nor more than 950° C. to substantial equilibrium by completion of reaction, and treating said source material with a reactant taken from the group consisting of saturated steam, a mildly acidic aqueous solution, and a mixture of saturated steam and a mildly acidic aqueous solution.

* * * * *